US00PP16749P3

(12) United States Plant Patent
van Straalen et al.

(10) Patent No.: US PP16,749 P3
(45) Date of Patent: Jul. 4, 2006

(54) ***ASTER* PLANT NAMED 'CEFORTUNA'**

(50) Latin Name: *Aster novi-belgii L.*
Varietal Denomination: Cefortuna

(75) Inventors: Harry W.M. van Straalen, Rijsenhout (NL); Wilfried J. Poland, Wervershoof (NL)

(73) Assignee: Chrysanthemum Breeders Association N.V. (NL)

( * ) Notice: Subject to any disclaimer, the term of this patent is extended or adjusted under 35 U.S.C. 154(b) by 89 days.

(21) Appl. No.: 10/979,190

(22) Filed: Nov. 3, 2004

(65) Prior Publication Data

US 2006/0095999 P1 May 4, 2006

(51) Int. Cl.
*A01H 5/00* (2006.01)

(52) U.S. Cl. ..... Plt./355

(58) Field of Classification Search ..... Plt./355
See application file for complete search history.

(56) References Cited

PUBLICATIONS

UPOV–ROM GTITM, Plant Variety Database, 2005/01, GTI Jouve Retrieval Software, Citation for Aster 'Cefortuna'.*

*Chrysanthemum* Breeders Association N.V. [online], [retrieved on Jun. 1, 2005]. Retrieved from the Internet <http://www.cbanv.nl/index.cfm>, 3 pages only.*

* cited by examiner

*Primary Examiner*—Anne Marie Grunberg
*Assistant Examiner*—June Hwu
(74) *Attorney, Agent, or Firm*—Steptoe & Johnson LLP

(57) ABSTRACT

An *Aster* plant named 'Cefortuna' characterized by its medium sized blooms with purple ray-florets and yellow disc florets, which can be propagated by means of cuttings from cuttings and produced with a short period.

3 Drawing Sheets

RELATED CULTIVARS

'Cefortuna' is developed from a breeding program for pot *asters* that has so far yielded the commercial varieties 'Dynaster' (U.S. Plant Pat. No. 15,262), 'Diamaster' (U.S. Plant Patent Application Ser. No. 10/426,847) and Dukaster (U.S. Plant Pat. No. 15,100).

BACKGROUND OF THE INVENTION

'Cefortuna' is a product of a breeding-program that had the objective of creating new *Aster* cultivars, that can be grown as pot plants and propagated by means of cuttings from cuttings, similar to the cultivation and propagation of all year round *chrysanthemum*. The new plant of the present invention comprises a new and distinct cultivar of an *Aster* plant. 'Cefortuna' is a seedling from a cross of a breeding program maintained at *Chrysanthemum* Breeders Association Research BV, Rijsenhout, Holland. The female parent is 97.6128, a non-commercialized *aster* variety; the male parent is unknown, being a mixed population of a group of male parents. A comparison with parent *aster* 97.6128 is also given in this application. The new and distinct cultivar was discovered and selected as a flowering plant within the progeny of the stated cross by Harry W. M. van Straalen in a controlled environment (greenhouse) in Rijsenhout, Holland in 2000. The first act of asexual reproduction of 'Cefortuna' was accomplished when vegetative cuttings were propagated from the initial selection in 2000 in a controlled environment in Rigsenhout, Holland.

SUMMARY OF THE INVENTION

The present invention 'Cefortuna' is a new and distinct variety of *Aster* bearing medium sized blooms with purple ray-florets and yellow disc florets, which can be propagated by a cutting from a cutting and produced as pot plants in 8 weeks time.

BRIEF DESCRIPTION OF THE DRAWINGS

The present invention 'Cefortuna' of a new and distinct variety of *Aster* is shown in the accompanying drawings, the color being as nearly true as possible with color photographs of this type.

DESCRIPTION OF THE INVENTION

Figure 1:
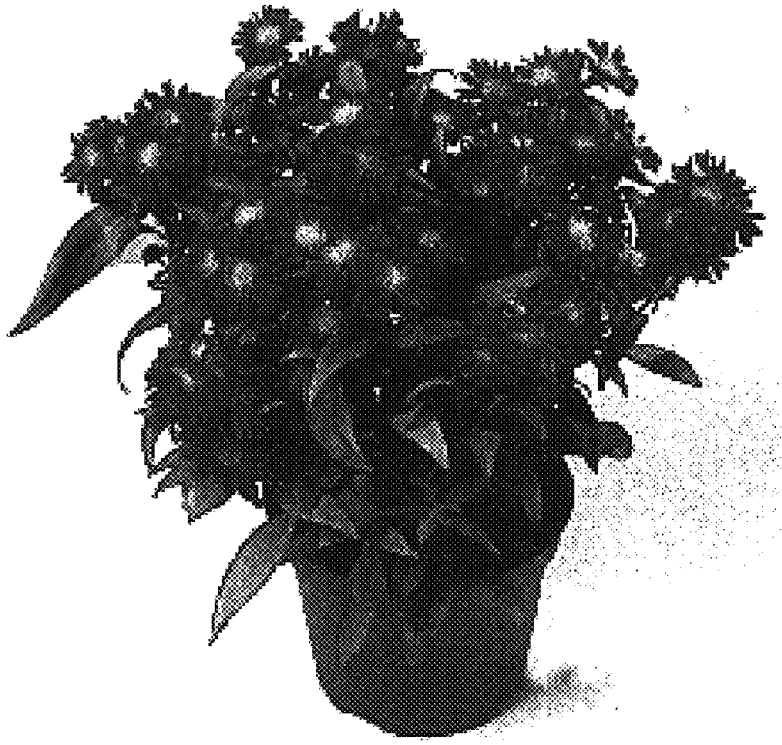
FIG. 1 shows a plant of the cultivar in full bloom.
Figure 2:
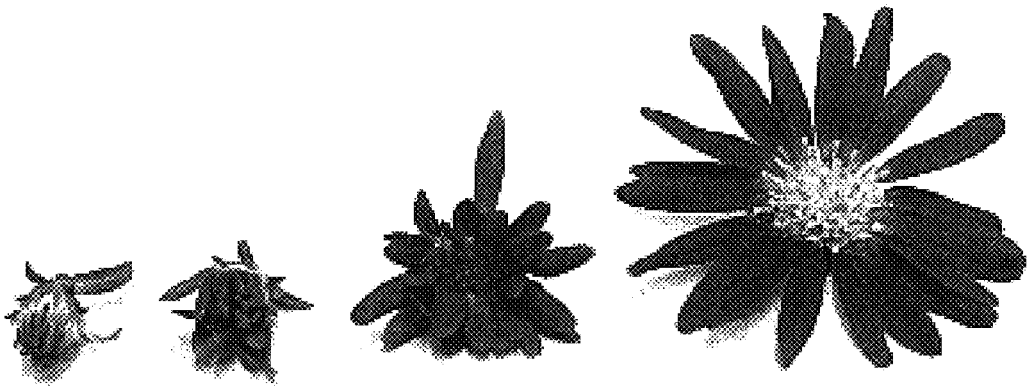
FIG. 2 shows the various stages of bloom of the new cultivar.
Figure 3:
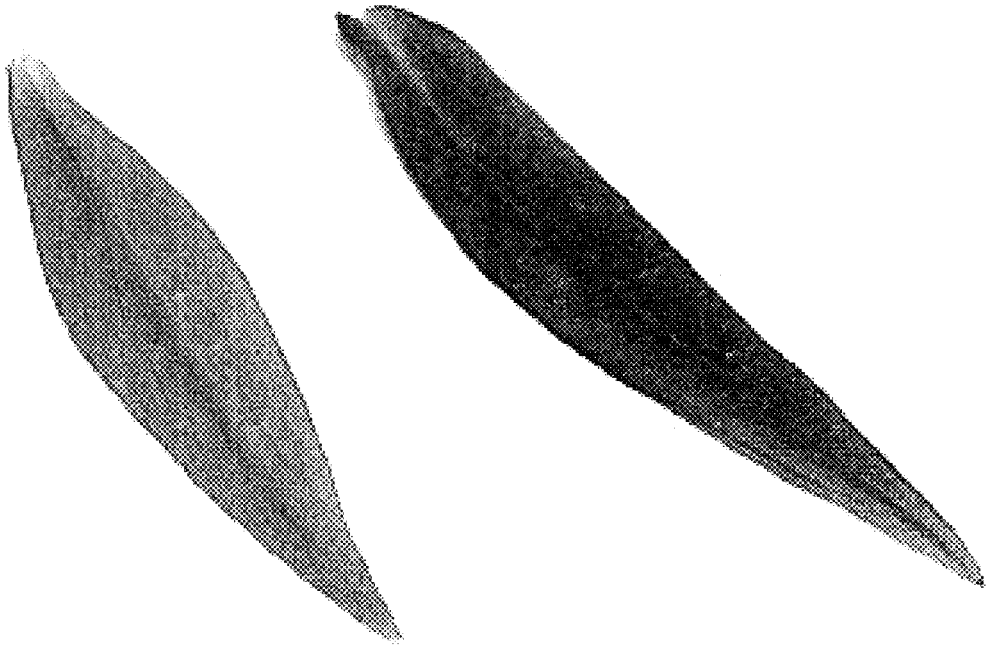
FIG. 3 shows the foliage of the new cultivar.

This new variety of *Aster* is of the botanical classification *Aster novi-belgii* L. The observations and measurements were gathered from plants grown in a greenhouse in Rijsenhout Holland in a photo-periodic controlled crop under conditions generally used in commercial practice. The greenhouse temperatures during this crop were at day-time between 18° C. and 25° C. and at night 20° C. The photo-periodic response time in this crop was 39 days, after an average of 16 long days after sticking of the unrooted cuttings. Plants are pinched 10 days after sticking. Growth retardants were applied in an average dose of 1.5 gram/liter water, starting one week after pinching. The plants were observed (directly) during the flowering of this crop. The plant is susceptible to Powdery Mildew. No tests were done on cold or drought tolerance. This new variety produces medium sized blooms with purple ray-florets andyellow disc-florets blooming on the plant for 4 weeks. This new variety of *Aster* has been found to retain its distinctive characteristics throughout successive propagations, however the phenotype may vary significantly with variations in environment such as light intensity and temperature. 'Cefortuna' can be planted with assimilation lightning (high pressure sodium lamps) between week 5 and week 35 under greenhouse conditions in Holland.

From the cultivars known to inventor the most similar existing cultivar in comparison to 'Cefortuna' are its female parent 97.6128 and the varieties 'Dukaster' and 'Dynaster'. When these varieties are being compared with 'Cefortuna' the following differences are noticed: The differences between 'Cefortuna', 97.6128, 'Dukaster' and 'Dynaster' are (1) Flower color. (2) Growth habit. (3) Leaf width. (1) The color of the ray-florets of 'Cefortuna' is purple, while it is pink in 'Dukaster' and violet in 97.6128 and 'Dynaster'. (2) The growth habit is upright and partially spreading in 'Cefortuna', while this is upright in 97.6128, 'Dukaster' and 'Dynaster' (3) The leaves of 'Cefortuna' and 'Dynaster' are of intermediate width, while those of 97.6128 are smaller, and those of 'Dukaster' are broader.

The following is a description of the plant and characteristics that distinguish 'Cefortuna' as a new and distinct variety. The color designations are taken from the plant itself. Accordingly, any discrepancies between the color designations and the colors depicted in the photographs are due to photographic tolerances. The color chart used in this description is: The Royal Horticultural Society Colour Chart, edition 1995.

TABLE 1

Botanical Description of cultivar 'Cefortuna'

| | |
|---|---|
| Bud | |
| Size | Medium, Cross-section 0.3 cm, height 0.5 cm |
| Outside color | Purple-violet 81C |
| Involucral bracts | 2 rows, length 4 mm, width 3 mm |
| Involucral bracts among disc-florets | Not present |
| Involucral bracts color | Green 138 D |
| Bloom | |
| Type | Daisy |
| Size | Medium |
| Fully expanded | 2.5–3 cm |
| Number of blooms per branch | 10–12 |
| Peduncle strength | Strong |
| Peduncle structure | Hairy with ribs |
| Peduncle length | 3 cm |
| Peduncle color | Green 139 B |
| Peduncle angle | 45* |
| Performance on the plant | 4 weeks |
| Seeds | Produced in small quantities, oval/ovate shaped, grey-brown 199 A, 1 mm. in length |
| Color | |
| Center of the bloom (disc-florets) | Immature Yellow-green 150C<br>Mature Yellow 1A |

TABLE 1-continued

Botanical Description of cultivar 'Cefortuna'

| | |
|---|---|
| Color of the ray-florets | Upper surface: Red-purple 72B<br>Lower surface: Purple-violet 81C |
| Tonality from Distance | A pot *aster* with purple flowers and a yellow disc |
| Color of the upper surface of the ray-florets after aging of the plant | Red-purple 72C |
| Ray florets | |
| Number of whorls of ray-florets | 2 |
| Texture | Upper and under side smooth |
| Number of ray-florets | 20–30 |
| Shape in cross-section | Straight |
| Curvature of longitudinal axis | Flat |
| Length of corolla tube | 0.3 cm |
| Ray-floret length | 1.5 cm |
| Ray-floret width | 0.2 cm |
| Shape of tip | Pointed |
| Shape of apex | Acute |
| Disc florets | |
| Disc diameter | 0.7 cm; 1 cm when styles of outer disc florets are included |
| Distribution of disc florets | Numerous, clearly visible at all stages of flowering |
| Shape | Tubular |
| Length | 0.6 cm |
| Color | Yellow-green 145 D |
| Reproductive Organs | |
| Stamen | Present in Disc florets only (1 per floret) |
| Stamen color | Yellow 13 A |
| Pollen color | Yellow-orange 14 A |
| Pistil | Present on both Ray- and Disc-florets (1 per floret) |
| Style color | Yellow-green 150 D |
| Style length | 0.6 cm |
| Ovaries | Enclosed in calyx |
| Calyx shape | Pappus |
| Calyx length | 0.4 cm |
| Calyx color | Yellow-green 150 D |
| Plant | |
| Form | A pot *aster* meant for indoor use |
| Growth habit | Upright and partially spreading |
| Growth rate | Vigorous |
| Height | 22 cm |
| Width | 17 cm |
| Internode length | 1.5–2 cm |
| Stem diameter | 2–3 mm |
| Stem color | Green 139 B |
| Stem strength | Strong |
| Stem brittleness | Not brittle |
| Stem anthocyanin coloration | Absent |
| Length of lateral branch | From top to bottom 18 cm |
| Lateral branch color | Green 139 B |
| Lateral branch, attachment | 30–40* |
| Branching (average number of lateral branches) | Medium with 3 breaks after pinching |
| Internode length | 1 cm |
| Flowering Response (photo-periodic controlled crop, not natural season) | 39 Days |
| Foliage | |
| Leaf arrangement | Alternate |
| Color immature stage | Upper side Yellow-green 144 C<br>Under side Yellow-green 146 D |
| Color mature stage | Upper side Green 137 B<br>Under side Green 139 C |
| Color Midvein | Upper side Yellow-green 147 D<br>Under side Yellow-green 147 C |
| Size | Medium; length 5–7 cm, width 1–1.5 cm |

TABLE 1-continued

| Botanical Description of cultivar 'Cefortuna' | |
|---|---|
| Quantity (number per lateral branch) | 12 |
| Shape | Elliptic |
| Texture upper side | Glabrous |
| Texture under side | Glabrous |
| Venation arrangement | Pinnately netted |
| Shape of the margin | Sinuate |
| Shape of Base | Attenuate |
| Apex | Acuminate |

TABLE 2

| | Differences with the comparison varieties | | | |
|---|---|---|---|---|
| | 'Cefortuna' | 97.6128 | 'Dukaster' | 'Dynaster' |
| Color upper side ray-florets | Red-purple 72B | Violet-blue 92A | Purple-violet 81A | Violet-blue 90A |
| Growth habit | Upright and spreading | Upright growing | Upright growing | Upright growing |
| Leaf width | 1–1.5 cm | 0.6–1.2 cm | 2 cm | 1.5 cm |

I claim:

1. A new and distinct variety of *Aster* plant as described and illustrated.

* * * * *